United States Patent [19]

Irwin

[11] Patent Number: 5,202,410
[45] Date of Patent: Apr. 13, 1993

[54] POLYIMIDES FROM SUBSTITUTED BENZIDINE

[75] Inventor: Robert S. Irwin, Wilmington, Del.

[73] Assignee: E. I. Du Pont de Nemours and Company, Wilmington, Del.

[21] Appl. No.: 783,703

[22] Filed: Oct. 21, 1991

[51] Int. Cl.$^5$ .............................................. C08G 69/12
[52] U.S. Cl. .................................... 528/327; 528/183; 528/184; 528/188; 528/220; 528/229; 528/310; 528/331; 528/353
[58] Field of Search ............... 528/327, 331, 310, 183, 528/184, 188, 220, 229, 353

[56] References Cited

U.S. PATENT DOCUMENTS

| 3,386,965 | 6/1968 | Huffman et al. | 260/78 |
| 3,533,997 | 10/1970 | Angelo | 528/327 |
| 4,837,299 | 6/1989 | Peters et al. | 528/353 |
| 5,026,819 | 6/1991 | Irwin | 528/329.1 |

OTHER PUBLICATIONS

"Aromatic Copolyamides Containing Pendant Carboxyl Groups", Hinderer et al., Applied Polymer Symposium, No. 21, 1-9 (1973).
Macromolecules 1985, 18, pp. 1058-1068.

*Primary Examiner*—Harold D. Anderson

[57] ABSTRACT

Certain substituted benzidines enable the preparation of linear chain, high molecular weight polyimides based on benzidine.

7 Claims, No Drawings

POLYIMIDES FROM SUBSTITUTED BENZIDINE

BACKGROUND OF THE INVENTION

Linear chain high molecular weight polyimides which are required for fibers and films cannot be formed from 2,2'-dicarboxybenzidine and pyromellitic dianhydride by the conventional polyamide-acid prepolymer route in dimethylacetamide because the pendant carboxyl groups participate in transamidation equilibration reactions in solution. This results in a highly solvophilic, extremely branched polyamide-acid which interferes both with spinning because of an inadequate rate of coagulation upon extrusion into a non-solvent and formation of a high molecular weight, linear polyamide-acid with pendant carboxyl groups. Pendant carboxyl groups afford (a) a mechanism for interchain hydrogen bonding and (b) enhanced solubility such that the polymer may be converted largely to imide form without losing the solubility needed for processing. The present invention avoids these problems.

SUMMARY OF THE INVENTION

This invention provides a new group of substituted aromatic diamines of the formulas

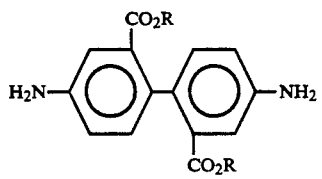

and

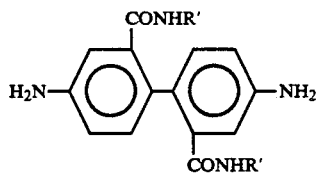

wherein R is lower primary or secondary alkyl (1–6 carbon atoms) and R' is methyl or ethyl. Also encompassed by this invention are polyimides of such diamines or mixtures of such diamines with a diamine of the group of p-phenylene diamine, 4,4'-diamino-diphenyl ether and 3,4'-diaminodiphenylether with a dianhydride selected from the group of pyromellitic dianhydride, biphenyldianhydride, benzophenone dianhydride, oxydiphthalic dianhydride and 2,2'-bis(3',4'-dicarboxyphenyl) hexafluoropropane. The polyimides comprise repeat units of the formula

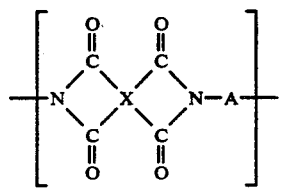

where X is

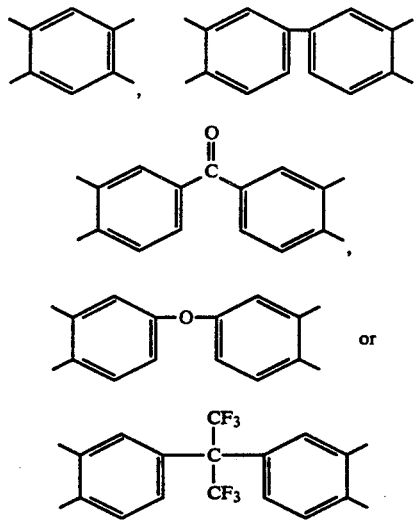

and where A is

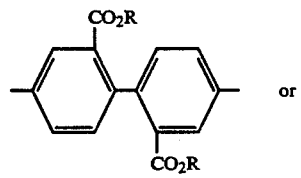

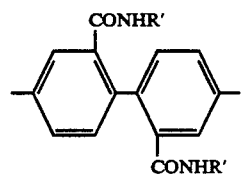

and mixtures thereof with

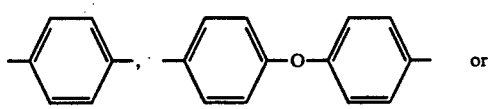

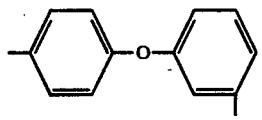

where R is 1–6 carbon primary or secondary alkyl and R' is methyl or ethyl. These polyimides may be heated at or above 300° C. to eliminate the —CO$_2$R or —CONHR' groups.

DETAILED DESCRIPTION OF THE INVENTION

In the well-known condensation of dianhydride with diamines to form solutions of polyamide-acids, as polyimide precursors, transamidation reactions occur between free carboxyl and polymer amide groups as discussed in Rees et al., Polym. Mat. Sci. and Eng., 60, 17 (1989). There is, however, no resulting change in chain linearity. When additional carboxyl groups are present as preformed substituents on one of the monomers, as in the polymerization of 2,2'-dicarboxylbenzidine with pyromellitic dianhydride (PMDA), in N-methylpyrrolidone (NMP) or similar solvent, these also can participate in transamidations, to give undesirably branched, extremely solvophilic material, which presents problems in coagulation in a wet-spinning process. The use of carboalkoxy or carboamide groups avoids this problem. In polyimide technology, as typified by the polypyromellitimide of

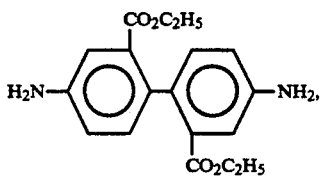

the presence of carboalkoxy groups facilitates spinning, and strength build-up. By heating to a higher temperature than is needed to imidize the fiber, the $-CO_2C_2H_5$ groups may be pyrolized to carbon dioxide and ethylene to leave the unsubstituted poly(biphenylene pyromellitimide) with attendant greater thermal stability. Moreover, the use benzidine, a known carcinogen, is avoided.

As diamine reactants which can be employed are

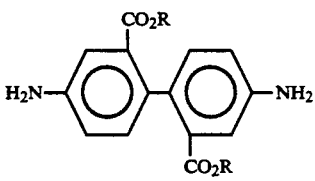

where R is 1-6 carbon primary or secondary alkyl, preferably methyl or ethyl, or

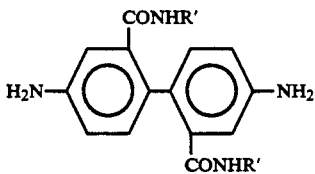

where R is methyl or ethyl. Such diamines may be copolymerized with a diamine of the group of p-phenylene diamine, 4,4'-diamino-diphenyl ether and 3,4'-diamino diphenyl ether to give copolyimides.

The aromatic dianhydrides which can be employed are pyromellitic dianhydride, biphenyldianhydride, benzophenone dianhydride, oxydiphthalic dianhydride and 2,2-bis[3',4'-bis(dicarboxyphenyl] hexafluoropropane.

The polyimides of the invention may be prepared from aromatic tetracarboxylic acid and aromatic diamine by the procedure described in U.S. Pat. No. 4,640,972 or from aromatic diamines and diacyl halides of aromatic tetracarboxylic acid diesters as described in U.S. Pat. No. 3,312,663. Both procedures are illustrated below in the examples.

TEST AND MEASUREMENTS

Thermogravimetric analysis measurements are made on a TA Instruments Inc. (Du Pont Instruments) Model 2950 Thermal Gravimetric Analyzer under nitrogen at a heating rate of 20° C./min.

The following examples are submitted to illustrate the invention and are not intended as limiting.

EXAMPLE 1

Dimethyl-4,4'-diaminodiphenate

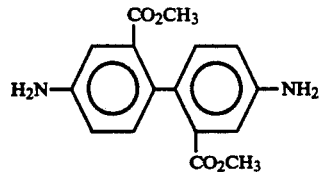

HCl gas was bubbled through a refluxing solution of 4,4'-diaminodiphenic acid (100 g) in methanol (3300 ml) for 15 hr; then refluxing was continued 42 hr. further without HCl. The cooled reaction mixture was filtered to provide crude dihydrochloride of dimethyl-4,4'-diaminodiphenate. A further crop was obtained by concentrating the methanolic mixture. The combined yields (119 g) were freed from a minor amount of insolubles and isolated as the free diamine by dissolving in water, filtering, and basifying with dilute $NH_4OH$ to pH 10. The filtered product (75 g; m.p. 115°-119° C.; 118° C. by DSC) presumably a hydrate was recrystallized from MeOH (8X) to dimethyl-4,4'-diaminodiphenate, m.p. 147°-9° C. by DSC; 98.54% purity by liquid chromatography (yield, 61 g, 55%). Azeotropic distillation from the dried solid by toluene did not separate any perceptible amount of water but raised the m.p. to 148°-150° C.

EXAMPLE 2

Diethyl-4,4'-diaminodiohenate

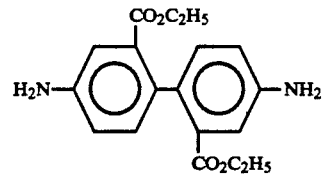

4,4'-Dinitrodiphenic acid may be prepared by known procedures [H. R. Patel, D. W. Blackburn, and G. L. Jenkins, J. Amer. Pharm. Assoc., 46 51 (1957).

A stirred solution of 4,4'-dinitrodiphenic acid (250 g, 0.753 mol.), ethanol (6 l.), and sulfuric acid (25 ml) was heated under reflux using a Soxhlet apparatus containing 4 Angstrom molecular sieves for 5 days. The diethyl-4,4'-dinitrodiphenate which separated was filtered off and dried, then recrystallized from acetone (8 l.) (240 g, 82% yield; m.p. 172-3° C.).

A mixture of diethyl-4,4'-dinitrophenate (182.5 g, 0.47 mol.), $PtO_2$(5.0 g), and ethyl acetate (12 l.) was hydrogenated for 10 hours at room temperature, giving theoretical uptake of hydrogen. After stirring 1 hour, the mixture was filtered through Celite to separate the catalyst. The filtrate was concentrated in vacuo to an oil. This was diluted with hydrochloric acid (120 ml) and the solid, which separated by filtration, and was recrystallized from water:acetone (1:4), had an m.p. 198°-200° C. (with decomposition). Elemental, infrared, and NMR analyses confirmed the composition to be diethyl-4,4'-diaminodiphenate dihydrochloride monohydrate, $C_{18}H_{24}Cl_2N_2O_5$, M.W. 419.

To isolate free diamine, the foregoing material (90 g, 0.215 mol) was dissolved in a minimal amount of water at 50° C., then slowly basified with a solution of sodium hydroxide (17 g; 0.425 equiv.). The precipitated product was filtered, washed free from base, and then dried at 80° C. under nitrogen (m.p. 125.5°–127.5° C.; yield 75 g). Elemental analysis showed that the product was anhydrous diethyl-4,4′-diaminodiphenate, $C_{18}H_{20}N_2O_4$.

EXAMPLE 3

4,4′-Diamino-N,N′-dimethyldiphendiamide 4,4′-Dinitrodiphenic acid (Patel et al., v.s.) (500 g, 1.5 mol.), thionyl chloride (2 kg, 16.8 mol.), and 1 drop of pyridine was heated under reflux for 6 hours. 4,4′-Dinitrodiphenoyl chloride was isolated as a crystalline residue by removal of thionyl chloride by distillation.

The crude 4,4′-dinitrodiphenoyl chloride (theoretically 1.5 mol.) dissolved in 1000 ml. tetrahydrofuran, was added dropwise to a 40% aqueous solution of methylamine (1750 ml) cooled at 15° C., and stirring continued at room temperature overnight. The separated, aqueous layer was extracted with ethyl acetate (twice with 2000 ml), the combined extracts washed with water (twice with 500 ml), dried over anhydrous $MgSO_4$, then concentrated in vacuo. The separated 4,4′-dinitro-N,N′-dimethyldiphendiamide was collected and dried, m.p. 238–240° C., yield 505 g (94%).

4,4′-Dinitro-N,N′-dimethyldiphendiamide (386.6 g, 1.079 mol.) $PtO_2$ (5 g.), ethanol (10 l.), water (2 l.) and conc. HCl (216 mol.) was hydrogenated until the theoretical amount of hydrogen was absorbed at room temperature (0.5 hr; 60 psi). After a further ½ hr. stirring, the mixture was diluted with water (4 l.), filtered through Celite to remove catalyst, and concentrated in vacuo. The precipitate was collected, dried, and recrystallized from a mixture of water, hydrochloric acid and acetone (thus, 2 g solid was dissolved in 10 ml water and 10 drops conc. HCl, the solution decolorized by charcoal (0.2 g), then diluted to turbidity by acetone). Yield of product (two crops) was 358 g (89%), m.p. 196°–200° C. Elemental, NMR, and infrared analysis showed 99.9% purity for 4,4′-diamino-N,N′-dimethyldiphendiamide·2HCl·2.3$H_2O$ ($C_{16}H_{18}N_4O_2$·2HCl·2.3 $H_2O$, M.W. 412.7).

Anhydrous, free diamine was isolated by the same procedure as for diethyl-4,4′-diaminodiphenate, in 83% yield, m.p. 274°–277° C.

EXAMPLE 4

Homopolymer prepared from dimethyl-2,2′-diaminodiphenate and 2,5-dicarbomethoxy terephthaloyl chloride, and conversion to the pyromellitimide is described schematically below.

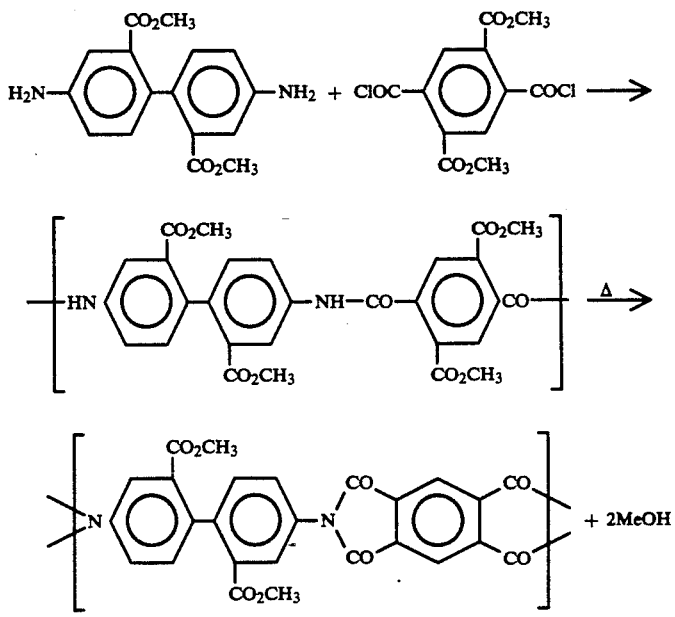

2,5-DiCarbomethoxy terephthaloyl chloride may be prepared by the procedure of Nishizaki and Moriwaki in Chem. Soc. Japan Journal (Ind. Chem. Section) 71, 1559–1564 (1968).

To a stirred anhydrous solution of dimethyl-2,2′-diaminodiphenate (6.59 g; 0.0220 mole) in NMP (100 ml) at about 10° C., under a slow supernatant flow of dry nitrogen, was added 2,5-dicarbomethoxy terephthaloyl chloride (7.01 g; 0.0220 mole). The clear solution, initially formed, gave way to a solid mass with a waxy consistency. The polymer was isolated by treatment with cold water in excess. Inherent viscosity in sulfuric acid was 2.98. It was converted to polyimide form by heating at 300° C. for 30 min.

EXAMPLE 5

Polyamideacid and polyimide are prepared from diethyl-4,4′-diaminodiphenate and pyromellitic dianhydride.

Diethyl-4,4′-diaminodiphenate (14.104 g; 0.043 mole) in anhydrous NMP (130 ml), under a slow flow of nitrogen, was treated with stirring with pre-dried pyromellitimide dianhydride (9.093 g, 0.0417 mole, 97% of theory) to form a low molecular weight polyamide-acid solution of modest viscosity. This was treated portionwise with a solution-slurry of PMDA (0.56 g) (15 ml) until solution viscosity had attained the desired viscosity. Dilution to 13% with a further 20 ml-NMP was required to reduce viscosity to a consistency suitable for film casting. Inherent viscosity by dilution of NMP to 0.5% concentration was 2.48. The solution could be readily precipitated by treatment with water.

A clear, almost colorless film was cast on a clear glass plate using a 0.015 in. doctor's knife and dried at 55° C. overnight. It was converted to polyimide form by successively heating for 30 minute periods at 200° C., and 300° C. The product was a light orange, highly flexible film having strong infrared absorption at 1780 cm$^{-1}$ characteristic of polyimides. It could be stretched over a heated plate at 400° C. When the film was heated for 20 min., at 400' C., the infrared spectrum was profoundly changed to indicate absence of CO$_2$Et or CO$_2$H groups. Weight loss by TGA corresponded to qualitative elimination of CO$_2$Et as CO$_2$+C$_2$H$_4$.

EXAMPLE 6

Polyamide-acid and polyimide are prepared from 4,4'-diamino-N,N'-dimethyldiphenamide and PMDA.

As in Example 5, 4,4'-diamino-N,N'-dimethyldiphenamide (20.58 g, 0.0698 mole) in DMAc (220 g) was treated with pyromellitic dianhydride PMDA (theoretically 15.20 g, 0.0698 mole) to provide a highly viscous, clear, light yellow solution (14%). Inherent viscosity by dilution of a specimen to 0.5% concentration by DMAc was 2.37, and remained unchanged during 2 days at room temperature. Dilution to 10% solids by 100 ml DMAc provided a consistency suitable for film casting. A clear film was obtained by casting on a clean glass plate with a 0.015 in. doctor's knife, dried at 70° C. for 15 hours under nitrogen. It was treated with isopropanol to release from the glass, then imidized by heating at 300° C. for 20 minutes.

EXAMPLE 7

Polyimide prepared from diethyl-4,4'-diaminodiphenate and biphenyldianhydride (BPDA).

To a stirred solution of 10.562 g. diethyl-4,4'-diaminodiphenate (0.0322 mole) in anhydrous DMAc (80.0 ml; 75.0 g.) was added 9.183 g. biphenyl dianhydride (0.0312 mole; 97% of theory) at 21° C. Then in a solution slurry containing 0.57 g. BPDA and 10 ml DMAc was added portionwise to provide the desired solution viscosity. After storing overnight in a refrigerator, this 20% polyamide-acid solution had gelled. It was fluidized by dilution to 15% solids and heating/stirring at 60° C. Inherent viscosity by dilution to 0.5% concentration was 2.26 in DMAc.

Films were cast using a 0.015 in. doctor's knife, dried at 100° C. for 2 hr. in a forced air oven, then imidized by heating for 30 min. each at 200°, 250°, and 300° C. The film changed from colorless to light yellow. When heated at 20° C./min. to 400° C. in nitrogen and held at 400° C. for 5 min., films became a deep orange brown.

I claim:

1. A polyimide comprising repeat units of the formula

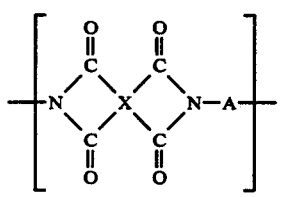

where X is

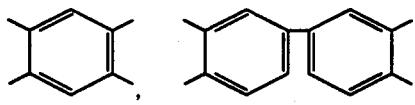

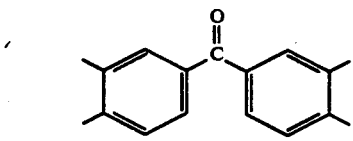

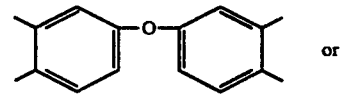, or

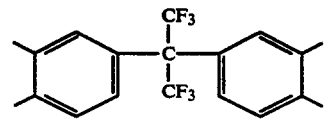

and where A is

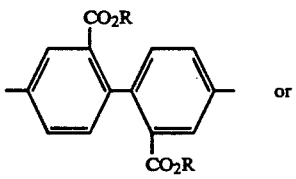 or

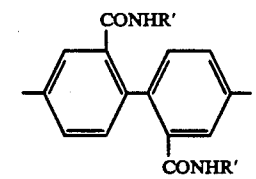

and mixtures thereof with

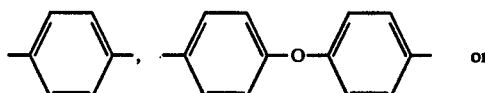

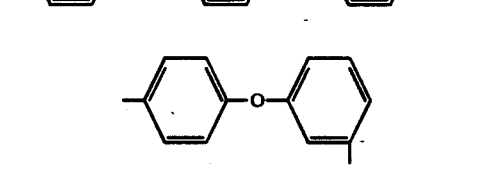

where R is 1-6 carbon primary or secondary alkyl and R' is methyl or ethyl.

2. A polyimide according to claim 1 wherein

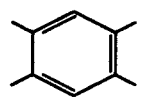

and A is

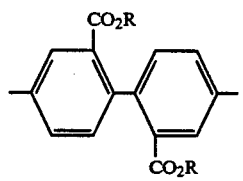
where R is 1-6 carbon atom primary or secondary alkyl.
3. A pyromellitimide of claim 2 wherein R is methyl.
4. A pyromellitimide of claim 2 wherein R is ethyl.
5. A polyimide according to claim 1 wherein -X is-
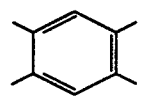
and A is
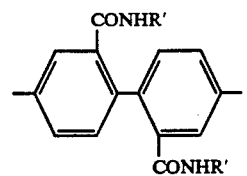
where R' is methyl.
6. A polyimide according to claim 1 where X is
and where A is
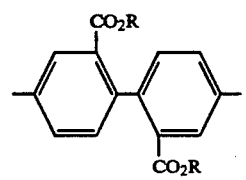
and where R is 1-6 carbon primary or secondary alkyl.
7. Fiber or film of the polyamide of claims 1 or 5.
* * * * *

UNITED STATES PATENT AND TRADEMARK OFFICE
CERTIFICATE OF CORRECTION

PATENT NO. : 5,202,410
DATED : April 13, 1993
INVENTOR(S) : Robert Samuel Irwin

It is certified that error appears in the above-identified patent and that said Letters Patent is hereby corrected as shown below:

Claim 2, column 8, line 60, after "wherein" insert --X is--.

Signed and Sealed this

Twenty-second Day of February, 1994

Attest:

BRUCE LEHMAN

*Attesting Officer*    *Commissioner of Patents and Trademarks*